United States Patent
Desos et al.

(10) Patent No.: US 7,494,995 B2
(45) Date of Patent: Feb. 24, 2009

(54) PHENYLPYRIDYLPIPERAZINE COMPOUNDS

(75) Inventors: Patrice Desos, Bois-Colombes (FR); Alexis Cordi, Suresnes (FR); Pierre Lestage, La Celle-Saint-Cloud (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 207 days.

(21) Appl. No.: 11/432,787

(22) Filed: May 11, 2006

(65) Prior Publication Data

US 2006/0258671 A1 Nov. 16, 2006

(30) Foreign Application Priority Data

May 12, 2005 (FR) .................... 05 04757

(51) Int. Cl.
*A61K 31/4418* (2006.01)
*C07D 213/72* (2006.01)
*C07D 213/74* (2006.01)

(52) U.S. Cl. .............. 514/235.8; 514/253.01; 514/253.09; 514/253.13; 544/121; 544/360; 544/364

(58) Field of Classification Search .......... None
See application file for complete search history.

(56) References Cited

U.S. PATENT DOCUMENTS

2003/0236259 A1* 12/2003 Hohlweg et al. ............ 514/242

FOREIGN PATENT DOCUMENTS

| EP | 0361489 | 4/1990 |
| WO | 92/05156 | 4/1992 |
| WO | 99/21834 | 5/1999 |

OTHER PUBLICATIONS

Phillips et al. Annual Reports in medicinal Chemistry, vol. 33, p. 31-40 (1998).*
Passani et al. Neuroscience and Biobehavioral Reviews, vol. 24, p. 107-113 (2000).*
Leurs et al. TIPS, vol. 19, p. 177-183 (1998).*
Philippu, et al., *Behav. Brain Res.*, 2001, 124, 151-159.
Bacciottini, et al., *Behav. Brain Res.*, 2001, 124, 183-194.
Alvarez, et al., *Behav. Brain Res.*, 2001, 124, 195-202.
Kim, et al., *Neuroscience Letters*, 2002, 321, 169-172.
Leurs, et al., *TiPS*, 1998, vol. 19, 177-183.
Tozer, et al., *Exp. Opin. Ther. Patents*, 2000, 10, 1045-1055.
Passani, et al., *Neurosci. Biobehav. Rev.*, 2000, 24, 107-113.
Fox, et al., *J. Pharm. Exper. Ther.*, 2003, 305, 897-908.
Ligneau, et al., *J. Pharm. Exper. Ther.*, 1998, 287, 658-666.
Monti, et al., *Eur. J. Pharmacol.*, 1991, 205, 283-287.
Stark, et al., *Drugs of the Future*, 1996, 21, 507-520.
Howard, *Exp. Opin. Ther. Patents*, 2000, 10, 1549-1559.
Itoh, et al., *Biol. Psychiatry*, 1999, 45, 475-481.
Masaki, et al., *Diabetes*, 2001, 50, 376-384.
Masaki, et al., *Endocrinology*, 2003, 144, 2741-2748.
Rouleau, et al., *J. Pharm. Exper. Ther.*, 1997, 281, 1085-1094.

* cited by examiner

*Primary Examiner*—Emily Bernhardt
(74) *Attorney, Agent, or Firm*—Hueschen and Sage

(57) ABSTRACT

A compound selected from those of formula (I):

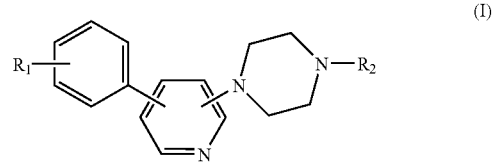

wherein:
$R_1$ represents an $NR_3SO_2R_4$ group wherein:
$R_3$ represents a hydrogen atom or an alkyl group,
$R_4$ represents an alkyl group, aryl group or $NR_5R_6$ group,
$R_2$ represents an alkyl, cycloalkyl or cycloalkylalkyl group,
and medicinal products containing the same which are useful in treating conditions treatable by antagonists of type $H_3$ central histamine receptors.

11 Claims, No Drawings

PHENYLPYRIDYLPIPERAZINE COMPOUNDS

The present invention relates to new phenylpyridylpiperazine compounds, to a process for their preparation and to pharmaceutical compositions containing them.

The compounds of the present invention are especially valuable from a pharmacological point of view because of their specific interaction with type $H_3$ central histamine receptors and can be used in the treatment of neuropathologies associated with cerebral ageing, mood disorders, eating behaviour and sleep-wakefulness rhythm, and of attention deficit hyperactivity syndrome.

Ageing of the population due to increased life expectancy at birth has brought with it a large increase in the incidence of age-related neuropathologies and especially of Alzheimer's disease. The principal clinical manifestations of cerebral ageing and especially of age-related neuropathologies are deficiencies in memory and cognitive functions, which may lead to dementia.

Recent neuropharmacological studies have shown that, in the central nervous system, histamine, via the central histaminergic systems, has the role of a neurotransmitter or neuromodulator in physiological or physiopathological situations (Annu. Rev. Neurosci., 1986, 9, 209-254; Physiol. Rev., 1991, 71, 1-51). Thus, it has been shown that histamine is involved in various physiological and behavioural processes, such as thermoregulation, neuro-endocrinal regulation, circadian rhythm, cataleptic states, motility, aggressiveness, eating behaviour, learning and memorisation, and synaptic plasticity (Hass et al., histaminergic neurones: morphology and function, Boca Raton, Fla.: CRC Press, 1991, pp. 196-208; Prog. Neurobiology, 2001, 63, 637-672).

Of the 3 histamine receptor sub-types ($H_1$, $H_2$ and $H_3$), it was initially shown that the type $H_3$ receptor is a pre-synaptic autoreceptor which controls the release of histamine (Nature, 1987, 327, 117-123). Its activation inhibits the release and synthesis of histamine by a negative feedback mechanism (Neuroscience, 1987, 23, 149-157). The existence of presynaptic heteroreceptors capable of modulating the release of some neuropeptides and of many neurotransmitters, such as noradrenaline, serotonin, dopamine, GABA, acetylcholine and glutamate, was demonstrated subsequently (TiPS, 1998, 19, 177-183). Studies carried out in animals have shown that an increase in endogenous extra-synaptic levels of histamine via blockage of type $H_3$ receptors by $H_3$ antagonists makes it possible to promote states of vigilance, learning and memory processes, to regulate food intake, and to combat convulsive attacks (Prog. Neurobiol., 2000, 63, 637-672; Neurosci. Biobehav. Rev., 2000, 24, 107-113). As a result, the potential therapeutic indications for $H_3$ antagonists are the treatment of cognitive deficiencies associated with cerebral ageing and with neurodegenerative diseases such as Alzheimer's disease, Parkinson's disease, Pick's disease, Korsakoff's disease and frontal or sub-cortical dementias of vascular or other origin, and the treatment of mood disorders, convulsive attacks, attention deficit hyperactivity syndrome, obesity, pain and narcoleptic states.

The compounds of the present invention, in addition to having a novel structure, have pharmacological properties which are entirely surprising and valuable in this field.

More specifically, the present invention relates to compounds of formula (I):

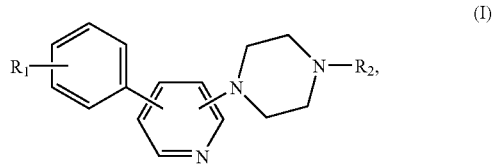

wherein
$R_1$ represents an $NR_3SO_2R_4$ group wherein:
  $R_3$ represents a hydrogen atom or a linear or branched ($C_1$-$C_6$)alkyl group,
  $R_4$ represents a linear or branched ($C_1$-$C_6$)alkyl group, an aryl group or an $NR_5R_6$ group wherein:
    $R_5$ and $R_6$, which may be the same or different, each represent a hydrogen atom or a linear or branched ($C_1$-$C_6$)alkyl group, a ($C_3$-$C_8$)cycloalkyl group or a ($C_3$-$C_8$)cycloalkyl-($C_1$-$C_6$)alkyl group in which the alkyl moiety is linear or branched, or $R_5$ and $R_6$, together with the nitrogen atom carrying them, form a 5- to 8-membered ring wherein one of the carbon atoms may be replaced by a nitrogen, oxygen or sulphur atom or by an SO or $SO_2$ group, the ring thereby defined optionally being bridged by a linear or branched ($C_1$-$C_6$)alkyl group and/or optionally being substituted by one or more identical or different groups selected from halogen, linear or branched ($C_1$-$C_6$)alkyl, linear or branched ($C_1$-$C_6$)alkoxy, linear or branched ($C_1$-$C_6$)polyhaloalkyl, carboxy, hydroxy, cyano, nitro and amino (optionally substituted by one or more linear or branched ($C_1$-$C_6$)alkyl groups),
$R_2$ represents a linear or branched ($C_1$-$C_6$)alkyl group, a ($C_3$-$C_8$)cycloalkyl group or a ($C_3$-$C_8$)cycloalkyl-($C_1$-$C_6$)alkyl group wherein the alkyl moiety may be linear or branched, it being understood that:
an aryl group means the groups phenyl, naphthyl and biphenyl, those groups optionally being substituted by one or more identical or different groups selected from halogen, linear or branched ($C_1$-$C_6$)alkyl, linear or branched ($C_1$-$C_6$)alkoxy, linear or branched ($C_1$-$C_6$)poly-haloalkyl, carboxy, hydroxy, cyano, nitro and amino (optionally substituted by one or more linear or branched ($C_1$-$C_6$)alkyl groups), to their enantiomers and diastereoisomers, and also to addition salts thereof with a pharmaceutically acceptable acid or base.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

More especially, the invention relates to compounds of formula (I) wherein $R_4$ represents an alkyl group, for example a methyl group.

Preference is given to the group $R_3$ being a hydrogen atom.

Advantageously, the invention relates to compounds of formula (I) wherein $R_5$ and $R_6$, together with the nitrogen atom carrying them, form a 5- to 8-membered ring wherein one of the carbon atoms may be replaced by a nitrogen, oxygen or sulphur atom or by an SO or $SO_2$ group, for example a morpholine group.

Preference is given to the $R_2$ group being an isopropyl, cyclopropyl or cyclopentyl group.

Even more especially, the invention relates to compounds of formula (I) which are:

N-{4-[6-(4-isopropylpiperazin-1-yl)pyridin-3-yl]phenyl}benzenesulphonamide dihydrochloride, N-{4-[6-(4-cyclopentylpiperazin-1-yl)pyridin-3-yl]phenyl}benzenesulphonamide dihydrochloride, N-[4-[6-(4-cyclopentyl-1-piperazinyl)-3-pyridinyl]phenyl]methanesulphonamide dihydrochloride, N-{4-[6-(4-cyclopropylpiperazin-1-yl)pyridin-3-yl]phenyl}methanesulphonamide dihydrochloride, N-{4-[6-(4-isopropylpiperazin-1-yl)pyridin-3-yl]phenyl}morpholine-4-sulphonamide dihydrochloride, N-{4-[6-(4-isopropylpiperazin-1-yl)pyridin-3-yl]phenyl}methanesulphonamide dihydrochloride, N-{4-[6-(4-isopropylpiperazin-1-yl)pyridin-3-yl]phenyl}propane-2-sulphonamide dihydrochloride, N-{4-[6-(4-cyclopentylpiperazin-1-yl)pyridin-3-yl]phenyl}-4-fluorobenzenesulphonamide dihydrochloride, N-{4-[6-(4-cyclopentylpiperazin-1-yl)pyridin-3-yl]phenyl}-3-fluorobenzenesulphonamide dihydrochloride, N-{4-[6-(4-cyclopentylpiperazin-1-yl)pyridin-3-yl]phenyl}-2-fluorobenzenesulphonamide dihydrochloride.

The invention relates also to a process for the preparation of compounds of formula (I), which process is characterised in that there is used, as starting material, the compound of formula (II):

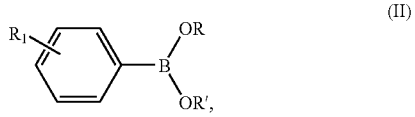

(II)

wherein $R_1$ is as defined for formula (I), and R and R', which may be the same or different, each represent a hydrogen atom or a linear or branched ($C_1$-$C_6$)alkyl group or together form a linear or branched ($C_1$-$C_6$)alkylene chain, which is condensed, in the presence of palladium(0), with a compound of formula (III):

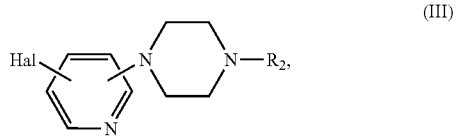

(III)

wherein $R_2$ is as defined for formula (I) and Hal represents a halogen atom, to yield the compound of formula (I), which compound of formula (I) is purified, if necessary, according to a conventional purification technique, is separated, where appropriate, into its isomers according to a conventional separation technique and is converted, if desired, into its addition salts with a pharmaceutically acceptable acid or base.

The compounds of formulae (II) and (III) as defined hereinbefore are either commercially available or obtained by conventional reactions of organic chemistry.

By virtue of their pharmacological properties as $H_3$ histamine receptor ligands, the compounds of the present invention are useful in the treatment of cognitive deficiencies associated with cerebral ageing and with neurodegenerative diseases, such as Alzheimer's disease, Parkinson's disease, Pick's disease, Korsakoff's disease and frontal or sub-cortical dementias of vascular or other origin, and also in the treatment of mood disorders, convulsive attacks, attention deficit hyperactivity syndrome, obesity, pain and narcoleptic states.

The present invention relates also to pharmaceutical compositions comprising as active ingredient at least one compound of formula (I), an isomer thereof or an addition salt thereof with a pharmaceutically acceptable acid or base, alone or in combination with one or more inert, non-toxic, pharmaceutically acceptable excipients or carriers.

Among the pharmaceutical compositions according to the invention, there may be mentioned more especially those that are suitable for oral, parenteral (intravenous, intramuscular or subcutaneous), per- or trans-cutaneous, intravaginal, rectal, nasal, perlingual, buccal, ocular or respiratory administration.

The pharmaceutical compositions according to the invention for parenteral injections especially include aqueous and non-aqueous sterile solutions, dispersions, suspensions or emulsions as well as sterile powders for the reconstitution of injectable solutions or dispersions.

The pharmaceutical compositions according to the invention for solid oral administration especially include tablets or dragées, sublingual tablets, sachets, capsules and granules, and for liquid oral, nasal, buccal or ocular administration especially include emulsions, solutions, suspensions, drops, syrups and aerosols.

The pharmaceutical compositions for rectal or vaginal administration are preferably suppositories, and those for per- or trans-cutaneous administration especially include powders, aerosols, creams, ointments, gels and patches.

The above-mentioned pharmaceutical compositions illustrate the invention but do not limit it in any way.

Among the inert, non-toxic, pharmaceutically acceptable excipients or carriers there may be mentioned, without implying any limitation, diluents, solvents, preservatives, wetting agents, emulsifiers, dispersants, binders, swelling agents, disintegrants, retardants, lubricants, absorbency agents, suspension agents, colourants, flavourings etc.

The useful dosage varies according to the age and weight of the patient, the route of administration, the pharmaceutical composition used, the nature and severity of the disorder, and whether any associated treatments are being taken. The dosage ranges from 10 mg to 1 g per day in one or more administrations.

The following Preparations and Examples illustrate the invention but do not limit it in any way. The starting materials used are known products or are prepared according to known procedures. The structures of the compounds described in the Examples were determined in accordance with the usual spectrophotometric techniques (infrared, NMR, mass spectrometry etc.).

Preparation 1

1-(5-Bromopyridin-2-yl)-4-isopropylpiperazine

A solution containing 12.1 g of 2,5-dibromopyridine (51.1 mmol), 8.8 ml of 1-isopropylpiperazine (61.5 mmol) and 9.2 ml of DBU (61.5 mmol) is stirred overnight at 100° C. The reaction mixture is returned to ambient temperature and the solution is diluted with water and extracted with ethyl acetate. The organic phases are collected, washed with brine, dried (MgSO₄) and evaporated under reduced pressure. The residue is chromatographed on an SiO₂ column, eluting with a mixture of CH₂Cl₂/MeOH 98/2 and then 96/4, to yield the title product.

Melting Point: 76-78° C.
Elemental Microanalysis:

|  | C | H | N | Br |
|---|---|---|---|---|
| %, theory | 50.72 | 6.38 | 14.79 | 28.12 |
| %, experiment | 50.96 | 6.47 | 14.53 | 28.33 |

Preparation 2

1-(5-Bromopyridin-2-yl)-4-cyclopentylpiperazine

Identical procedure to that of Preparation 1, but the 1-isopropylpiperazine is replaced by 1-cyclopentylpiperazine.
Melting Point: 127-128° C.

Preparation 3

1-(5-Bromopyridin-2-yl)-4-cyclopropylpiperazine

Identical procedure to that of Preparation 1, but the 1-isopropylpiperazine is replaced by 1-cyclopropylpiperazine.
Melting Point: 110-115° C.

EXAMPLE 1

N-{4-[6-(4-Isopropylpiperazin-1-yl)pyridin-3-yl]phenyl}benzene-sulphonamide dihydrochloride Step A: N-(4-Iodophenyl)benzenesulphonamide To a solution of 2.0 g of 4-iodoaniline (9.13 mmol) in 40 ml of acetonitrile there are added 1.48 ml of pyridine (18.26 mmol) and then, dropwise, a solution of 1.28 ml of benzenesulphonyl chloride (10 mmol) in 20 ml of acetonitrile. The reaction mixture is stirred overnight at ambient temperature and the acetonitrile is evaporated off under reduced pressure. The residue is taken up in 1N HCl and extracted with ethyl acetate. The organic phase is washed with brine, dried (MgSO₄) and evaporated under reduced pressure. The oily residue obtained is triturated in isopropyl ether until the title product crystallises.

Melting Point: 141-143° C.

Step B: N-[4-(4,4,5,5-Tetramethyl-1,3,2-dioxaborolan-2-yl)phenyl]benzene-sulphonamide 500 mg of the compound obtained in Step A (1.39 mmol), 389 mg of bis(pinacolato)diborane (1.53 mmol), 410 mg of potassium acetate (4.18 mmol) and 5 ml of dimethylformamide are introduced into a 25 ml two-necked flask. The reaction mixture is degassed by bubbling through a current of nitrogen for 30 minutes, and then 16 mg of palladium acetate (0.07 mmol) are added. The reaction mixture is stirred under a gentle current of nitrogen for 7 hours at 85° C. After cooling to ambient temperature, the reaction mixture is diluted with water and extracted with ethyl acetate. The organic phases are combined, washed with brine, dried and evaporated under reduced pressure. The residue from evaporation is triturated in heptane to yield, after filtration, the title product in the form of a white solid.

Melting Point: 157-160° C.

Step C: N-{4-[6-(4-Isopropylpiperazin-1-yl)pyridin-3-yl]phenyl}benzene-sulphonamide dihydrochloride 226 mg of the compound obtained in Preparation 1 (0.79 mmol), 300 mg of the compound obtained in Step B (0.83 mmol), 3 ml of dioxane and 3 ml of 0.4M aqueous Na₂CO₃ solution are introduced into a 25 ml two-necked flask. The reaction mixture is degassed by bubbling nitrogen through for 30 minutes. Pd(0) tetrakistriphenylphosphine (45 mg, 0.04 mmol) is introduced and the reaction mixture is stirred at 90° C. under a gentle current of nitrogen for 3 hours. After cooling to ambient temperature, the reaction mixture is diluted with water and extracted with ethyl acetate. The extracted phases are combined, washed with brine, dried (MgSO₄) and evaporated under reduced pressure. The residue obtained is chromatographed on SiO₂ (CH₂Cl₂/MeOH/NH₄OH 96/4/0.4) to yield the title product in the form of the base. The base is dissolved in ethereal HCl and then the solution is concentrated and filtered to yield the title product in the form of the hydrochloride.

Melting Point: 160-163° C.
Elemental Microanalysis:

|  | C | H | N | S | Cl |
|---|---|---|---|---|---|
| %, theory | 56.58 | 5.93 | 11.00 | 6.29 | 13.92 |
| %, experiment | 55.36 | 6.3 | 10.62 | 6.32 | 13.67 |

EXAMPLE 2

N-{4-[6(4-Cyclopentylpiperazin-1-yl)pyridin-3-yl]phenyl}benzene-sulphonamide dihydrochloride The product obtained in Step B of Example 1 is reacted with the compound obtained in Preparation 2, under the conditions described in Step C of Example 1.

Melting Point: 162-167° C.
Elemental Microanalysis:

|  | C | H | N | S | Cl |
|---|---|---|---|---|---|
| %, theory | 58.31 | 6.02 | 10.46 | 5.99 | 13.24 |
| %, experiment | 58.71 | 6.05 | 10.53 | 6.03 | 12.66 |

EXAMPLE 3

N-[4-[6-(4-Cyclopentyl-1-piperazinyl)-3-pyridinyl]phenyl]methane-sulphonamide dihydrochloride Step A: N-(4-Iodophenyl)methanesulphonamide Identical procedure to Step A of Example 1, but the benzenesulphonyl chloride is replaced by methanesulphonic anhydride.

Melting Point: 118-120° C.
Elemental Microanalysis:

| | C | H | N | S | I |
|---|---|---|---|---|---|
| %, theory | 28.30 | 2.71 | 4.71 | 10.79 | 42.71 |
| %, experiment | 28.67 | 2.83 | 4.70 | 11.22 | 43.44 |

Step B: N-[4-(4,4,5,5-Tetramethyl-1,3,2-dioxaborolan-2-yl)phenyl]methane-sulphonamide Identical procedure to Step B of Example 1, but starting from the product obtained in Step A above.
Melting point: 180-182° C.

Step C: N-[4-[6-(4-Cyclopentyl-1-piperazinyl)-3-pyridinyl]phenyl]methane-sulphonamide dihydrochloride Identical procedure to Step C of Example 1, starting from the product obtained in Step B and replacing the compound obtained in Preparation 1 by the compound obtained in Preparation 2.
Melting Point: 227-229° C.
Elemental Microanalysis:

| | C | H | N | S | Cl |
|---|---|---|---|---|---|
| %, theory | 53.27 | 6.39 | 11.83 | 6.77 | 14.98 |
| %, experiment | 53.22 | 6.41 | 11.43 | 6.85 | 14.89 |

EXAMPLE 4

N-{4-[6-(4-Cyclopropylpiperazin-1-yl)pyridin-3-yl]phenyl}methane-sulphonamide dihydrochloride The product obtained in Step B of Example 3 is reacted with the compound obtained in Preparation 3, under the conditions described in Step C of Example 1.
Melting Point: 197° C.
Elemental Microanalysis:

| | C | H | N | S | Cl |
|---|---|---|---|---|---|
| %, theory | 51.24 | 5.88 | 12.58 | 7.20 | 15.92 |
| %, experiment | 51.70 | 5.78 | 12.21 | 6.81 | 15.93 |

EXAMPLE 5

N-{4-[6-(4-Isopropylpiperazin-1-yl)pyridin-3-yl]phenyl}morpholine-4-sulphonamide dihydrochloride Step A:
N-(4-Iodophenyl)morpholine-4-sulphonamide To a solution of 10 g of 4-iodoaniline (45.6 mmol) in 200 ml of acetonitrile there are added 6.41 ml of Et$_3$N (45.6 mmol) and 8.47 g of morpholine-4-sulphonyl chloride (45.6 mmol). The reaction mixture is stirred for 16 hours at ambient temperature. The acetonitrile is evaporated off in vacuo, and the residue is taken up in 1N HCl and extracted with CH$_2$Cl$_2$.
The organic phases are combined, washed with brine, dried (MgSO$_4$) and treated with animal charcoal to yield the title product.
Melting Point: 91° C.

Step B: N-[4-(4,4,5,5-Tetramethyl-1,3,2-dioxaborolan-2-yl)phenyl]morpholine-4-sulphonamide Identical procedure to Step B of Example 1, starting from the product obtained in Step A.
Melting Point: 158-161° C.

Step C: N-{4-[6-(4-Isopropylpiperazin-1-yl)pyridin-3-yl]phenyl}morpholine-4-sulphonamide dihydrochloride Identical procedure to Step C of Example 1, starting from the product obtained in Step B.
Melting Point: 194-198° C.
Elemental Microanalysis:

| | C | H | N | S | Cl |
|---|---|---|---|---|---|
| %, theory | 50.96 | 6.41 | 13.51 | 6.18 | 13.67 |
| %, experiment | 50.90 | 6.79 | 13.23 | 6.09 | 13.46 |

EXAMPLE 6

N-{4-[6-(4-Isopropylpiperazin-1-yl)pyridin-3-yl]phenyl}methane-sulphonamide dihydrochloride The product of Step B of Example 3 is reacted with the compound obtained in Preparation 1, under the conditions described in Step C of Example 1.
Melting Point: 191° C.
Elemental Microanalysis:

| | C | H | N | S | Cl |
|---|---|---|---|---|---|
| %, theory | 50.19 | 6.25 | 12.32 | 7.05 | 17.15 |
| %, experiment | 50.14 | 6.10 | 11.49 | 6.58 | 17.25 |

EXAMPLE 7

N-{4-[6(4-Isopropylpiperazin-1-yl)pyridin-3-yl]phenyl}propane-2-sulphonamide dihydrochloride Step A: N-(4-Iodophenyl)propane-2-sulphonamide
Identical procedure to Step A of Example 5 replacing morpholine-4-sulphonyl chloride with propane-2-sulphonyl chloride.
Melting Point: 96° C.
Elemental Microanalysis:

| | C | H | N | S | I |
|---|---|---|---|---|---|
| %, theory | 33.24 | 3.72 | 4.31 | 9.86 | 39.03 |
| %, experiment | 33.21 | 3.38 | 4.17 | 9.74 | 38.37 |

Step B: N-[4-(4,4,5,5-Tetramethyl-1,3,2-dioxaborolan-2-yl)phenyl]propane-2-sulphonamide Identical procedure to Step B of Example 1, starting from the product obtained in Step A.

Melting Point: 192° C.

Elemental Microanalysis:

|  | C | H | N | S |
|---|---|---|---|---|
| %, theory | 55.40 | 7.44 | 4.31 | 9.86 |
| %, experiment | 55.46 | 7.33 | 4.54 | 10.11 |

Step C: N-{4-[6-(4-Isopropylpiperazin-1-yl)pyridin-3-yl]phenyl}propane-2-sulphonamide dihydrochloride Identical procedure to Step C of Example 1, starting from the product obtained in Step B.

Melting Point: 165° C.

Elemental Microanalysis:

|  | C | H | N | S | Cl |
|---|---|---|---|---|---|
| %, theory | 53.05 | 6.78 | 11.78 | 6.74 | 14.91 |
| %, experiment | 53.05 | 7.07 | 11.58 | 6.47 | 14.62 |

EXAMPLE 8

N-{4-[6-(4-Cyclopentylpiperazin-1-yl)pyridin-3-yl]phenyl}4-fluorobenzenesulphonamide dihydrochloride Step A: {4-[6-(4-Cyclopentylpiperazin-1-yl)pyridin-3-yl]phenyl}amine Identical procedure to Step C of Example 1, using [4-(4,4,5,5-tetramethyl-1,3,2-dioxaborolan-2-yl)phenyl]amine.

Melting Point: 160-162° C.

Step B: N-{4-[6-(4-Cyclopentylpiperazin-1-yl)pyridin-3-yl]phenyl}-4-fluorobenzenesulphonamide dihydrochloride A suspension containing 200 mg (0.620 mmol) of the product obtained in Step A and 302 mg (1.55 mmol) of 4-fluorophenylsulphonic acid chloride in 2 ml of pyridine is stirred for 3 hours at 80° C. After cooling to ambient temperature, the reaction mixture is precipitated by adding water. The precipitate is collected by filtration, dissolved in a mixture of $CH_2Cl_2$/MeOH, absorbed onto about 1 g of silica and chromatographed on a silica column, eluting with a mixture of $CH_2Cl_2$/MeOH/$NH_3$ 98/2/0.2. The dihydrochloride is formed by taking up the base in ethanol and adding ethereal HCl.

Melting Point: 256-262° C.

Elemental Microanalysis:

|  | C | H | N | S | Cl |
|---|---|---|---|---|---|
| %, theory | 56.42 | 5.64 | 10.12 | 5.79 | 12.81 |
| %, experiment | 56.03 | 5.73 | 9.77 | 5.45 | 12.74 |

EXAMPLE 9

N-{4-[6-(4-Cyclopentylpiperazin-1-yl)pyridin-3-yl]phenyl}-3-fluorobenzene-sulphonamide dihydrochloride Identical procedure to Example 8, but using 3-fluorophenylsulphonic acid chloride in Step B.

Melting Point: 167-170° C.

Elemental Microanalysis:

|  | C | H | N | S | Cl |
|---|---|---|---|---|---|
| %, theory | 56.42 | 5.64 | 10.12 | 5.79 | 12.81 |
| %, experiment | 56.72 | 5.60 | 9.96 | 5.67 | 12.86 |

EXAMPLE 10

N-{4-[6-(4-Cyclopentylpiperazin-1-yl)pyridin-3-yl]phenyl}-2-fluoro-benzenesulphonamide dihydrochloride Identical procedure to Example 8, but using 2-fluorophenylsulphonic acid chloride in Step B.

Melting Point: 248-253° C.

Elemental Microanalysis:

|  | C | H | N | S | Cl |
|---|---|---|---|---|---|
| %, theory | 56.42 | 5.64 | 10.12 | 5.79 | 12.81 |
| %, experiment | 56.46 | 5.63 | 9.87 | 5.47 | 12.80 |

Pharmacological Study of Compounds of the Invention

Example A

Cerebral Levels of $N^\tau$-Methylhistamine in the NMRI Mouse

The purpose of this study, which was carried out in accordance with the method of Taylor et al. (Biochem. Pharm., 1992, 44, 1261-1267), is to evaluate the ex vivo activity of the compounds of the present invention as antagonists of type $H_3$ central histamine receptors. That activity is revealed by measuring, after treatment intraperitoneally with the test compounds, the central levels of $N^\tau$-methylhistamine, which is a main metabolite of histamine. An increase in the cerebral concentrations of $N^\tau$-methylhistamine indicates an increase in the turn-over of histamine by blockage of the type $H_3$ central histamine receptors.

NMRI mice (18-20 g) are treated intraperitoneally or orally with compounds of the present invention or with their carrier (20 ml/kg). One hour after the pharmacological treatment, the animals are sacrificed, and their brains are removed, frozen in liquid nitrogen, weighed and homogenised in 0.1N $HClO_4$ at 4° C. The homogenised products are centrifuged (15 000 g, 17 min, 4° C.). The supernatants are recovered and divided into aliquots. The aliquots are frozen in liquid nitrogen and stored at −80° C. until analysis.

Determination of the cerebral levels of $N^\tau$-methylhistamine is carried out by radio-immunological assay (RIA)

using an assay kit. The tissue levels of $N^\tau$-methylhistamine are expressed in µg/g of fresh brain. The comparison of the cerebral levels of $N^\tau$-methylhistamine between animals treated with the carrier (controls) and animals treated with compounds of the present invention is carried out by single-factor variance analysis followed, if necessary, by a complementary analysis (Dunnett's test).

The results show that, at doses of from 1 to 10 mg/kg PO, the compounds of the present invention are capable of increasing endogenous cerebral concentrations of $N^\tau$-methylhistamine by 100%.

By way of example, the compounds of Examples 4 and 7, administered at doses of 10 mg/kg and 3 mg/kg PO, respectively, allow an increase in the endogenous cerebral concentrations of $N^\tau$-methylhistamine of 162% and 138%, respectively, to be obtained.

These results demonstrate that the compounds of the present invention are powerful antagonists of type $H_3$ central histamine receptors.

Example B

Electroencephalographic Recordings on Freely Moving Rats

Adult male Wistar rats were chronically implanted with electrodes placed over the frontal and parietal cortex. Cortical electroencephalogram (EEG) was recorded from rats placed inside cages in a sound attenuating-room. Compounds and vehicle were administered in a random order at 10:00 AM on the same days with a minimum of 3 days between each administration, allowing each rat to serve as its own control. Absolute power of slow wave delta band activity (1-4 Hz), that predominates during slow wave sleep and disappears during wakefulness and rapid eyes movement sleep, was averaged over successive periods of 30 min. Over 30 min, low and high values of slow wave delta power are signs of arousal and sleep, respectively.

Results indicate that compounds of the present invention increase arousal (decrease of delta band activity) for doses ranging between 0.3 to 3 mg/kg IP.

Example C

Pharmaceutical Composition

| | |
|---|---|
| Preparation formula for 1000 tablets each containing a dose of 100 mg of N-[4-[6-(4-cyclopentyl-1-piperazinyl)-3-pyridinyl]phenyl]methanesulphonamide dihydrochloride (Example 3) | 100 g |
| Hydroxypropylcellulose | 2 g |
| Wheat starch | 10 g |
| Lactose | 100 g |
| Magnesium stearate | 3 g |
| Talc | 3 g |

We claim:
1. A compound selected from those of formula (I):

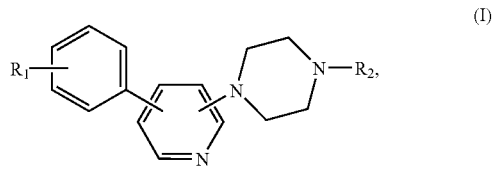

wherein:
$R^1$ represents an $NR_3SO_2R_4$ group wherein:
$R^3$ represents a hydrogen atom or a linear or branched ($C_1$-$C_6$)alkyl group,
$R^4$ represents a linear or branched ($C_1$-$C_6$)alkyl group, an aryl group or an $NR_5R_6$ group wherein:
$R_5$ and $R_6$, which may be the same or different, each represent a hydrogen atom, a linear or branched ($C_1$-$C_6$)alkyl group, a ($C_3$-$C_8$)cycloalkyl group, or a ($C_3$-$C_8$)cycloalkyl-($C_1$-$C_6$)alkyl group in which the alkyl moiety is linear or branched, or $R_5$ and $R_6$, together with the nitrogen atom carrying them, form a 5- to 8-membered ring wherein one of the carbon atoms may be replaced by a nitrogen, oxygen or sulphur atom or by an SO or $SO_2$ group, wherein the ring thereby defined is optionally bridged by a linear or branched ($C_1$-$C_6$)alkylene group and is optionally substituted by one or more identical or different groups selected from halogen, linear or branched ($C_1$-$C_6$)alkyl, linear or branched ($C_1$-$C_6$)alkoxy, linear or branched ($C_1$-$C_6$) polyhaloalkyl, carboxy, hydroxy, cyano, nitro and amino (optionally substituted by one or more linear or branched ($C_1$-$C_6$)alkyl groups),
$R_2$ represents a linear or branched ($C_1$-$C_6$)alkyl group, a ($C_3$-$C_8$)cycloalkyl group or a ($C_3$-$C_8$)cycloalkyl-($C_1$-$C_6$)alkyl group wherein the alkyl moiety may be linear or branched,
it being understood that:
an aryl group means phenyl, naphthyl and biphenyl, wherein such groups may be optionally substituted by one or more identical or different groups selected from halogen, linear or branched ($C_1$-$C_6$)alkyl, linear or branched ($C_1$-$C_6$)alkoxy, linear or branched ($C_1$-$C_6$) poly-haloalkyl, carboxy, hydroxy, cyano, nitro and amino (optionally substituted by one or more linear or branched ($C_1$-$C_6$)alkyl groups),
its enantiomers and diastereoisomers, and addition salts thereof with a pharmaceutically acceptable acid or base.

2. A compound of claim 1, wherein $R_4$ represents an alkyl group, its enantiomers and diastereoisomers, and addition salts thereof with a pharmaceutically acceptable acid or base.

3. A compound of claim 1, wherein $R_3$ represents a hydrogen atom, its enantiomers and diastereoisomers, and addition salts thereof with a pharmaceutically acceptable acid or base.

4. A compound of claim 1, wherein $R_5$ and $R_6$, together with the nitrogen atom carrying them, form a 5- to 8-membered ring wherein one of the carbon atoms may be replaced by a nitrogen, oxygen or sulphur atom or by an SO or $SO_2$ group, its enantiomers and diastereoisomers, and addition salts thereof with a pharmaceutically acceptable acid or base.

5. A compound of claim 1, wherein $R_2$ represents an isopropyl group, its enantiomers and diastereoisomers, and addition salts thereof with a pharmaceutically acceptable acid or base.

6. A compound of claim 1, wherein $R_2$ represents a cyclopropyl or cyclopentyl group, its enantiomers and diastereoisomers, and addition salts thereof with a pharmaceutically acceptable acid or base.

7. A compound of claim 1, which is N-[4-[6-(4-cyclopentyl-1-piperazinyl)-3-pyridinyl]phenyl]methanesulphonamide dihydrochioride, and addition salts thereof with a pharmaceutically acceptable acid or base.

8. A process for the preparation of the compounds of formula (I) of claim 1, wherein a compound of formula (II):

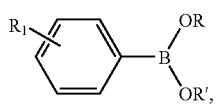

wherein R and R', which may be the same or different, each represent a hydrogen atom or a linear or branched ($C_1$-$C_6$)alkyl group or together form a linear or branched ($C_1$-$C_6$)alkylene chain, is condensed, in the presence of palladium(0), with a compound of formula (III):

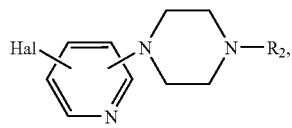

wherein Hal represents a halogen atom,
to yield the compound of formula (I),
which compound of formula (I) is purified, if necessary, according to a conventional purification technique, is separated, where appropriate, into its isomers according to a conventional separation technique and is converted, if desired, into its addition salts with a pharmaceutically acceptable acid or base.

9. A pharmaceutical composition comprising as active ingredient a compound of claim 1 in combination with one or more inert, non-toxic, pharmaceutically acceptable excipients or carriers.

10. A method for treating a living animal body, including a human, afflicted with a condition selected from convulsive attacks, attention deficit hyperactivity syndrome, obesity and narcoleptic states, comprising the step of administering to the living animal body, including a human, a compound of claim 1 which is effective for alleviation of the condition.

11. A method for treating a living animal body, including a human, afflicted with a condition selected from cognitive deficiencies associated with Alzheimer's disease, comprising the step of administering to the living animal body, including a human, a compound of claim 1 which is effective for alleviation of the condition.

\* \* \* \* \*